United States Patent
Pendharkar et al.

(10) Patent No.: US 7,186,684 B2
(45) Date of Patent: Mar. 6, 2007

(54) HEMOSTATIC DEVICE CONTAINING A PROTEIN PRECIPITATE

(75) Inventors: Sanyog M. Pendharkar, Old Bridge, NJ (US); Anne J. Gorman, Hightstown, NJ (US)

(73) Assignee: Ethicon, Inc., Somerville, NJ (US)

( * ) Notice: Subject to any disclaimer, the term of this patent is extended or adjusted under 35 U.S.C. 154(b) by 92 days.

(21) Appl. No.: 10/896,455

(22) Filed: Jul. 22, 2004

(65) Prior Publication Data

US 2005/0037051 A1   Feb. 17, 2005

Related U.S. Application Data

(60) Provisional application No. 60/493,117, filed on Aug. 7, 2003.

(51) Int. Cl.
   *C04B 24/26* (2006.01)
   *C07K 1/00* (2006.01)
   *A61K 38/00* (2006.01)

(52) U.S. Cl. .............................. 514/2; 530/350; 514/12
(58) Field of Classification Search ................ 530/350; 435/69.1; 514/12, 2
   See application file for complete search history.

(56) References Cited

U.S. PATENT DOCUMENTS 2,605,887 A   8/1952   Duncan
3,649,293 A * 3/1972   Hoer et al. .................. 426/431
4,789,733 A * 12/1988  Winkelman .................. 530/383
5,134,229 A * 7/1992   Saferstein et al. ............ 536/56
6,121,232 A   9/2000   Nur et al.

FOREIGN PATENT DOCUMENTS

WO   WO 92/13495 A1   8/1992

OTHER PUBLICATIONS

Merriam-Webster Online Dictionary publication, http://www.m-w.com/cgi-bin/dictionary?book=Dictionary&va=animal, Mar. 11, 2006.*

Badin et al., Selective chemical precipitation of serum proteins as an inexpensive tool for health screening and diagnosis, 1978, Ricerca in Clinica e in Laboratorio, vol. 8(Suppl. 1), pp. 183-193.*

* cited by examiner

Primary Examiner—Robert B. Mondesi (57) ABSTRACT

The present invention is directed to hemostatic devices comprising a substrate, which substrate comprises a precipitate of a protein in an amount effective to provide hemostatic properties to the substrate, or to maintain and/or improve hemostatic properties of the substrate, and to methods of making such devices, wherein the substrate comprising the precipitate of the protein is prepared by precipitation of the protein on or into the substrate upon contacting the protein with the substrate.

9 Claims, 5 Drawing Sheets

HEMOSTATIC DEVICE CONTAINING A PROTEIN PRECIPITATE

CROSS-REFERENCE TO RELATED APPLICATIONS

This application claims priority to U.S. provisional application Ser. No. 60/493,117 filed on Aug. 7, 2003.

FIELD OF THE INVENTION

This invention relates to a hemostatic device, e.g. a wound dressing, comprising a protein precipitate and to methods of making the device.

BACKGROUND Of THE INVENTION

Regenerated cellulose fabric that has been oxidized to contain carboxylic groups (CORC) is commonly used in preparing hemostatic wound dressings and is acidic in nature due to the presence of the carboxylic acid groups. Such fabrics include rayon fabrics that have been oxidized to include carboxylic groups. Examples of hemostatic oxidized regenerated cellulose absorbable hemostats commercially available include Surgicel® absorbable hemostat, a knitted fabric of oxidized regenerated cellulose (ORC), Surgicel Nu-Knit® absorbable hemostat, a dense ORC fabric and Surgicel® Fibrillar absorbable hemostat, mircrofibrils of ORC, all available from Johnson & Johnson Wound Management Worldwide, a division of Ethicon, Inc., Somerville, N.J., a Johnson & Johnson Company.

Such fabrics are believed to be incompatible with biological materials that may be sensitive to acidic environment. For instance, when thrombin is exposed to CORC fabrics it is known to rapidly lose its enzymatic activity. Previous attempts to make CORC compatible with enzymes and other proteins that otherwise are acid-sensitive have involved neutralizing CORC fabric or powder with calcium or sodium salts, or other neutralizing agents.

It would be advantageous to provide hemostatic wound dressings and medical devices utilizing such wound dressings that provide effective and/or improved hemostasis to a site of a body in need of hemostasis when compared to a conventional wound dressing, while allowing for the incorporation of materials that may be sensitive to acidic environment. The inventions described herein provide such advantages.

SUMMARY OF THE INVENTION

The present invention is directed to hemostatic devices comprising a substrate, which substrate comprises a protein precipitate in an amount effective to provide hemostatic properties to the substrate, or to maintain and/or improve hemostatic properties of the substrate, and to methods of making such devices, wherein the substrate comprising the protein precipitate is prepared by precipitation of the protein on or into the substrate upon contacting the protein with the substrate.

DETAILED DESCRIPTION OF THE INVENTION

In one embodiment, the present invention is directed to hemostatic devices comprising a substrate that comprises a protein precipitate in an amount effective to provide hemostatic properties to the substrate, or to improve and/or maintain hemostatic properties of the substrate. In certain embodiments, the protein precipitate may be formed simultaneously with contact of the protein with the substrate, thereby incorporating the protein precipitate on or into the substrate.

As used herein, "hemostatic", or "hemostatic properties", means the ability to stop or minimize bleeding, as one skilled in the art of hemostasis would understand those terms to mean, as further exemplified in the examples of the specification.

While it is not intended to be bound by the following theory, it is believed that protein precipitates according to the present invention are capable of binding to platelets and other cells in the body when placed in contact with blood of a body, as well as binding to other proteins and activating platelets. Binding to the platelets by the protein precipitate is believed to enhance hemostatic properties of fabrics that include the protein precipitate. In addition, enrichment of platelets caused by binding of the protein precipitate thereto may improve wound healing as platelets contain growth factors known to enhance wound healing. Binding of the protein precipitates also may stimulate cell growth for tissue engineering applications.

The protein precipitate may be prepared from proteins selected from the group consisting of fibrinogen, fibrin, fibronectin and Von Willebrand Factor. In certain embodiments the protein precipitate may be formed from a fibrin hydrogel formed by the combination of fibrinogen with thrombin. The protein used to prepare the protein precipitate may be human, animal or recombinant. Human derived proteins are described in PCT patent application WO/02/095019 A1 and U.S. Pat. Nos. 5,792,835 and 6,121,232, the contents each of which is incorporated by reference herein in its entirety.

In certain embodiments of the invention, wound dressings of the present invention comprise a fibrous fabric having a first surface and second surface opposing the first surface. The fabric comprises fibers and possesses physical properties suitable for use as a hemostat. Such properties include flexibility, strength and porosity. Fabrics utilized in the present invention may be woven or nonwoven, provided that the fabric possesses the physical properties necessary for application to a site of the body while maintaining its structural integrity and, preferably, although not necessarily, to provide hemostasis to the site. A preferred woven fabric has dense and knitted structure that provides form and shape for the hemostat.

The fibers used to prepare the fabric substrate comprise a biocompatible polymer. The fibers may be fabricated from any biocompatible polymer known for use in medical wound dressings. Dispersed at least on one of the surfaces of the fabric substrate that is to be placed in contact with the bleeding site, or in certain embodiments throughout the fabric, is the protein precipitate. The precipitate should be substantially uniformly distributed on the surface of the substrate in order to provide desired hemostatic properties, as excessive voids in the substrate where the precipitate is not present may comprise the hemostatic properties sought. In addition to the distribution of the precipitate, an amount of protein precipitate effective to provide and/or maintain and/or improve hemostatic properties of the wound dressing should be employed. By way of example, carriers, such as solutions or gels as described herein, may contain from 1–100 to 10–40 milligrams of protein per milliliter of carrier. It is noted that substantially all of the protein will precipitate from the carrier. Once having the benefit of this disclosure, one skilled in the art will be able to readily ascertain the particular amount of protein precipitate required per weight of substrate and the degree of uniformity required to achieve hemostatic properties of devices of the present invention.

In certain embodiments of the present invention, the absorbable hemostatic wound dressing comprises a warp knitted tricot fabric constructed of bright rayon yarn that is subsequently oxidized by known techniques to provide CORC. The fabrics are characterized by having a single ply thickness of at least about 0.5 mm, a density of at least about 0.03 g/cm$^2$, air porosity of less than about 150 cm$^3$/sec/cm$^2$ and liquid absorption capacity of at least about 3 times the dry weight of the fabric and at least about 0.1 g water per cm$^2$ of the fabric.

The knitted fabrics have good bulk without undue weight, are soft and drapable, conforming well to the configuration of the surface to which they are applied. The fabric may be cut into suitable sizes without running or fraying along the cut edge. Fabric strength after oxidation is more than adequate for use as a surgical hemostat.

Preferred hemostatic fabrics used in the present invention comprise CORC and are best characterized by their physical properties of thickness, bulk, porosity and liquid absorption capacity as recited above. Suitable fabrics having these properties may be constructed by knitting 60 denier, 18-filament bright rayon yarn on a 32-gauge machine at a knit quality of 12. A suitable tricot fabric construction is front-bar 1-0, 10-11; back-bar 2-3, 1-0. The extended shog movement imparted to the front bar results in a 188 inch runner compared to a 70 inch runner for the back guide bar and increases the fabric bulk and density. The ratio of front to back bar runners in this particular construction is 1:2.68.

Typical physical and hemostatic properties of fabrics produced as described above are noted in Table 1.

TABLE I

| Property | |
|---|---|
| Thickness (mm); | 0.645 |
| Density (g/cm$^2$); | 0.052 |
| Air Porosity (cm$^3$/sec/cm$^2$); | 62.8 |
| Tensile Strength[1](md/cd)Kg; | 1.9/4.5 |
| Elongation[2] (%); | 23/49 |

TABLE I-continued

| Property | |
|---|---|
| Absorption[3] | |
| (g/g fabric); | 3.88 |
| (g/cm$^2$ fabric); | 0.20 |
| Hemostasis[4] (min) | |
| 1 ply; | 5.7 ± 1.0 |
| 2 ply; | 5.6 ± 1.8 |

[1]tensile strength determined at 2 in/min extension md/cd = machine direction/cross direction.
[2]Elongation, machine direction/cross direction.
[3]Absorption based on weight of water absorbed by fabric.
[4]Hemostasis evaluation on incised porcine splenic wounds, time to stop bleeding.

The tricot fabrics utilized in the present invention may be constructed from bright rayon yarns of from about 40 to 80 total denier. Each yarn may contain from 10 to 25 individual filaments, although each individual filament is preferably less than 5 denier to avoid extended absorption times. The high bulk and fabric density are obtained by knitting at 28 gauge or finer, preferably at 32 gauge, with a fabric quality of about 10 or 12 (40 to 48 courses per inch). A long guide bar shog movement of at least 6 needle spaces, and preferably 8 to 12 spaces, further increases fabric thickness and density. Other warp knit tricot fabric constructions which produce equivalent physical properties may be utilized in the manufacture of the hemostatic fabrics and wound dressings of the present invention, and such constructions will be apparent to those skilled in the art once having the benefit of this disclosure.

Polymers useful in preparing fabrics and wound dressings of the present invention include, without limitation, chitosan, chitin, polysaccharides, polymethacrylic acids, polyamines, polyimines, polyamides, polyesters, polyethers, polynucleotides, polynucleic acids, polypeptides, proteins, poly(alkylene oxide), polythioesters, polythioethers, polyvinyls, polylactides, polyglycolides and copolymers or mixtures thereof. The polymers may be degradable or non-degradable, depending on whether the device comprising the fabric is contemplated for external or internal use. In certain embodiments, rayon fabric that has been oxidized to include either carboxylic moieties or aldehyde moieties may be used according to the present invention.

The wound dressing of the present invention remains very flexible, conforms to a bleeding site, and retains good tensile and compressive strength to withstand handling during application. The wound dressing can be cut into different sizes and shapes to fit the surgical needs. It can be rolled up or packed into irregular anatomic areas. The fabric in a preferred embodiment is a CORC, such as Surgicel Nu-Knit®, available from Ethicon, Inc., Somerville, N.J., although other fabrics may be utilized.

Where the substrate contains acidic moieties at levels sufficient to provide the appropriate acidic environment for causing the protein to precipitate out of the selected carrier, e.g. carboxylic moieties as contained in CORC, the protein precipitate may be formed simultaneously with contact of the protein and the fabric substrate and incorporated directly on the surface of and/or into the fabric substrate. The acidic environment typically will comprise a pH of from about 2.5 to about 6. Carriers that may be used to deliver the protein to be precipitated include solutions or gels.

In one embodiment, a solution containing fibrinogen was contacted with a CORC fabric substrate. The solution will contain from about 1 to about 100 milligram of fibrinogen per milliliter of solution, Upon contact of fibrinogen with the CORC fabric, fibrinogen precipitated out of solution onto the fabric substrate, thereby forming a fibrinogen pad comprising the fabric substrate having the fibrinogen precipitate incorporated therewith.

In another embodiment, a fibrin gel was first prepared by mixing fibrinogen and thrombin together at levels effective to provide hemostatic properties upon precipitation of the fibrin onto the substrate. The gel was then applied to a CORC fabric substrate and fibrin was shown to precipitate out of the gel in the presence of the CORC. The solid and liquid components of the gel were thereby separated and the solid, fibrin precipitate incorporated into the CORC fabric substrate. When utilized, thrombin may be animal, human or recombinant. Examples of human thrombin that may be utilized in the present invention are described in U.S. Pat. No. 5,143,838, the content of which is incorporated herein by reference in its entirety.

In both cases of a solution and a gel carrier, a hemostatic fibrin(ogen) pad containing precipitated fibrin(ogen) was formed by exposure of fibrin(ogen) to the carboxylic moieties of the fabric. The fibrin(ogen) pad thus formed had hemostatic properties that were as good as or better than and thus was as good as or better in promoting hemostasis in vivo than either a pad prepared from a fabric that did not contain acidic moieties and that was exposed to native fibrin(ogen), or a pad prepared from a CORC fabric that was not exposed to fibrinogen and thus did not include a fibrin (ogen) precipitate.

In embodiments where a solution or gel comprising the protein is applied to the substrate, the solution or gel first is prepared having a concentration of protein effective to provide, improve or maintain hemostasis when placed in contact with a substrate having acid moieties in amounts effective to provide an acidic environment suitable for causing the protein to precipitate out of the solution or gel. The solution or gel then is contacted with the substrate and allowed to remain in contact for a period of time sufficient to allow formation of the protein precipitate. Typically, precipitation of the protein is substantially simultaneous with contact and so contact time may be minimal. In certain embodiments the time of contact of the substrate with the protein may be up to about 30 minutes, or 45 minutes. The substrate comprising the protein precipitate then is dried to remove the liquid component of the solution or gel. In certain embodiments, removal of the liquid is conducted using lyophilization, whereby the liquid is frozen and then removed under vacuum.

Figure 1:
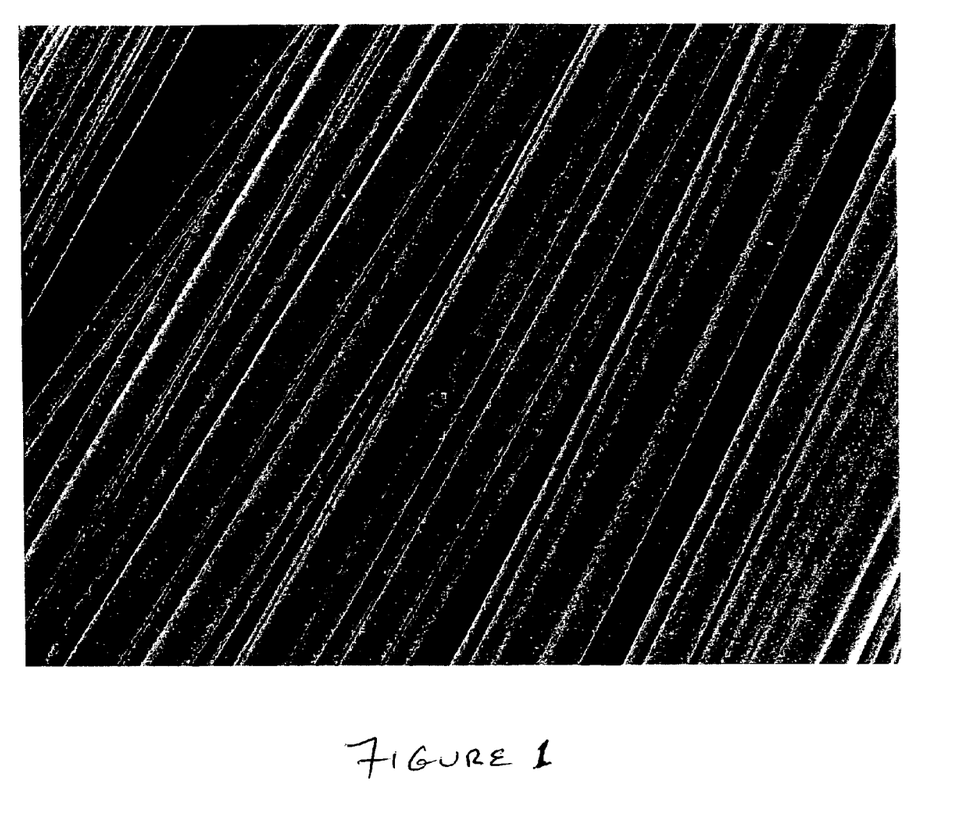
FIG. 1 is an image produced by scanning electron microscopy (1500×) of a surface of a comparative wound dressing.
Figure 2:
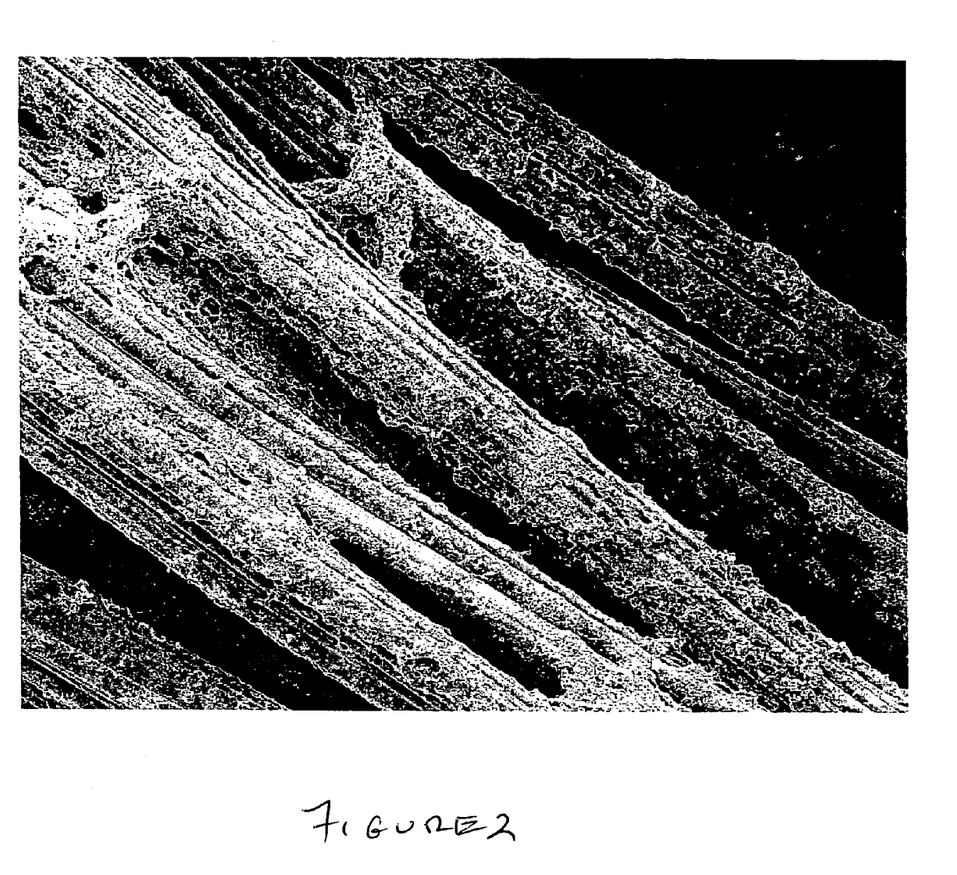
FIG. 2 is an image produced by scanning electron microscopy (1500×) of a surface of a comparative wound dressing.
Figure 3:
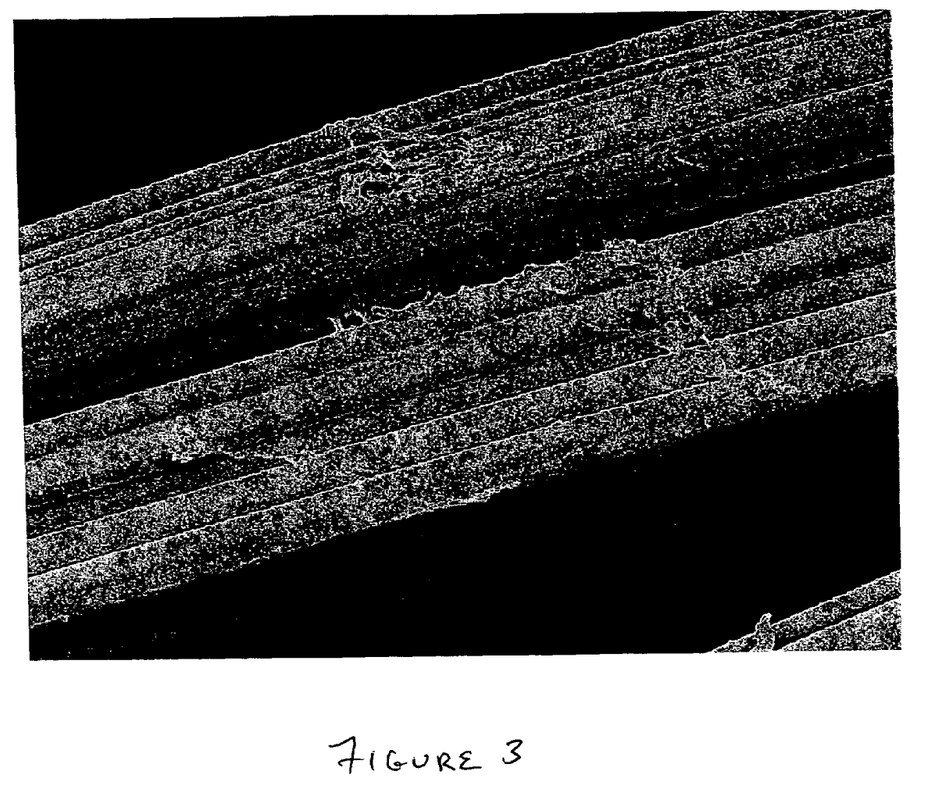
FIG. 3 is an image produced by scanning electron microscopy (1500×) of a surface of a comparative wound dressing.
Figure 4:
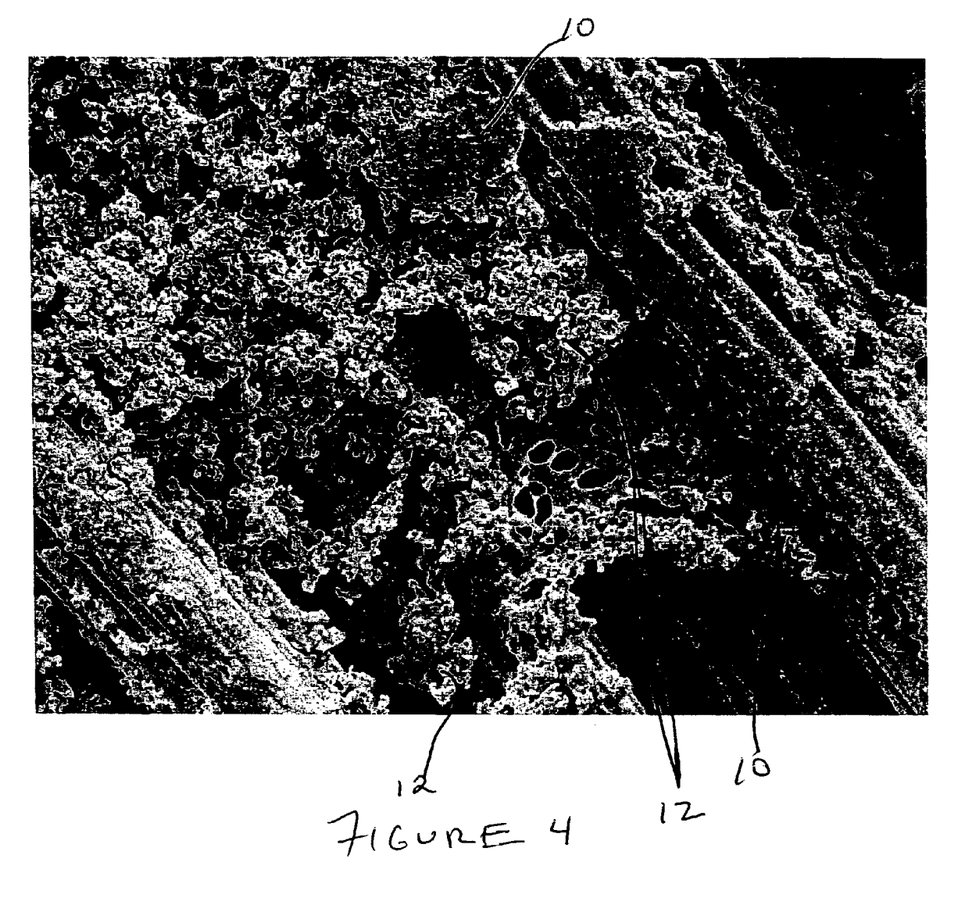
FIG. 4 is an image produced by scanning electron microscopy (1500×) of a surface of a wound dressing of the present invention.
Figure 5:
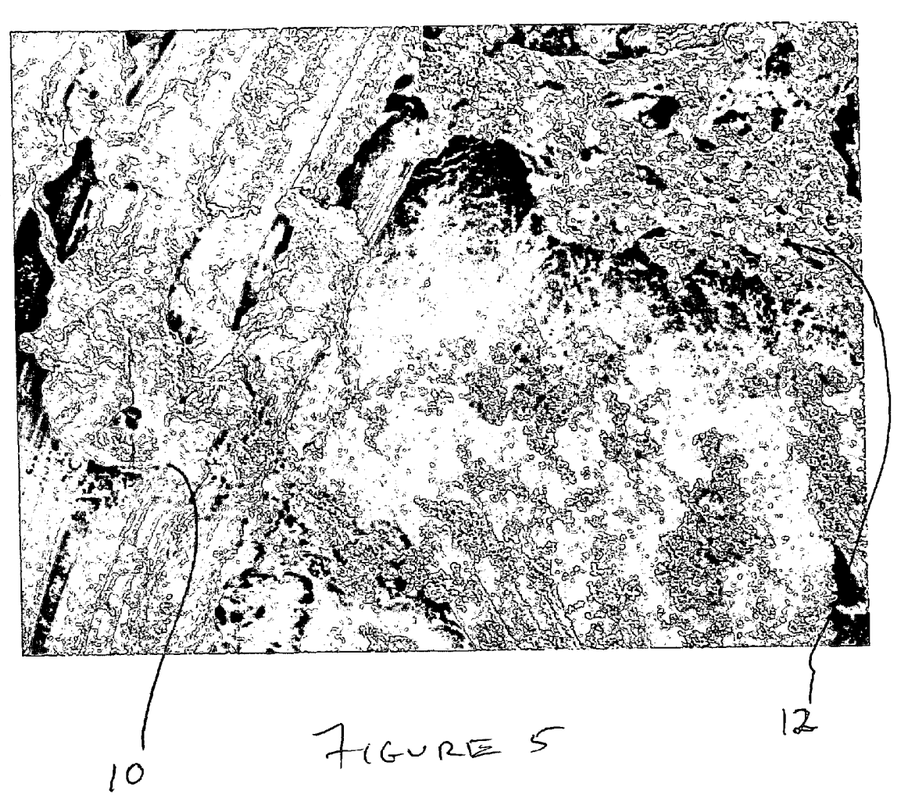
FIG. 5 is an image produced by scanning electron microscopy (750×) of a surface of a wound dressing of the present invention.

As seen in FIGS. 1–5, fabrics as described herein which have been reacted with Platelet Rich Plasma (PRP) as described in Example 8 are shown. FIG. 1 depicts a rayon fabric substrate that does not contain acidic moieties, has not been contacted with fibrinogen, but which was reacted with PRP as described in Example 8. FIG. 2 depicts a CORC fabric substrate as described herein that has not been contacted with fibrinogen, does not comprise a protein precipitate, but which was reacted with PRP as described in Example 8. FIG. 3 depicts a rayon fabric substrate containing no acidic moieties, that has been exposed to fibrinogen as prepared in Example 7b and reacted with PRP as described in Example 8. No precipitate is noted. FIGS. 4 and 5 depict a CORC substrate that has been contacted with fibrinogen as prepared in Example 7a and reacted with PRP as described in Example 8. As noted, fibrinogen precipitate 10 is shown to bind platelets 12 on the CORC fabric.

The following examples are provided in order to further exemplify embodiments of the present invention, and are not intended to limit the scope of the inventions.

EXAMPLE 1

Porcine Fibrinogen-Coated Rayon Pad

A 10×10 cm piece of rayon fabric (1.1 g) was placed in a plastic container and 10 ml of a solution of fibrinogen (Fraction 1 from pig plasma—40 mg/ml clottable protein in citrate buffered saline pH 6.8) was added to saturation. No precipitation of the fibrinogen was observed. The fabric was lyophilized and cut into 2.5×1.5 cm pieces for testing in a swine spleen hemostasis model.

EXAMPLE 2

Porcine Fibrinogen-Coated CORC Pad

A 10×10 cm piece of Surgicel®NuKnit wound dressing made from CORC rayon fabric (1.2 g) was placed in a plastic container and 10 ml of a solution of fibrinogen (Fraction 1 from pig plasma—40 mg/ml clottable protein in citrate buffered saline pH 6.8) was added to saturation. Immediate precipitation of the fibrinogen was observed. The fabric was lyophilized and cut into 2.5×1.5 cm pieces for testing in a swine spleen hemostasis model.

EXAMPLE 3

Porcine Fibrin-Coated Rayon Pad 10 ml of fibrinogen (Fraction 1 from pig plasma—40 mg/ml clottable protein in citrate buffered saline pH 6.8) was poured into a glass petri dish to cover the bottom of the dish. 1 ml of bovine thrombin (1000 u/ml) was added and the dish was gently swirled to mix the thrombin with the fibrinogen. A fibrin gel quickly formed. After approximately 10 minutes, a 10×10 cm piece of non-oxidized rayon fabric (1.0 g) was placed on top of the gel and allowed to sit at room temperature for approximately 30 minutes. No precipitation was observed. The fabric/gel composite was then lyophilized. Complete de-lamination of the fabric from the gel layer was observed. Therefore, no testing as described herein below was performed with this material.

EXAMPLE 4

Porcine Fibrin Coated CORC Pad 10 ml of fibrinogen (Fraction 1 from pig plasma—40 mg/ml clottable protein in citrate buffered saline pH 6.8) was poured into a glass petri dish to cover the bottom of the dish. 1 ml of bovine thrombin (1000 u/ml) was added and the dish was gently swirled to mix the thrombin with the fibrinogen. A fibrin gel quickly formed. After approximately 10 minutes, a 10×10 cm piece of Surgicel®NuKnit wound dressing made from CORC rayon fabric (1.3 g) was placed on top of the gel and allowed to sit at room temperature for approximately 30 minutes. Immediate precipitation within the gel layer was observed and the fabric sank into the gel, thus forming a composite of the gel and fabric. The composite was then lyophilized. The resulting material was then cut into 2.5×1.5 cm pieces and tested in a swine spleen hemostasis model.

EXAMPLE 5

Porcine Fibrin Coated CORC Pad 10 ml of fibrinogen (Fraction 1 from pig plasma—10 mg/ml clottable protein in citrate buffered saline pH 6.8) was poured into a glass petri dish to cover the bottom of the dish. 1 ml of bovine thrombin (1000 u/ml) was added and the dish was gently swirled to mix the thrombin with the fibrinogen. A fibrin gel quickly formed. After approximately 10 minutes, a 10×10 cm piece of Surgicel®NuKnit wound dressing made from CORC rayon fabric (1.1 g) was placed on top of the gel and allowed to sit at room temperature for approximately 30 minutes. Immediate precipitation within the gel was observed and the fabric sank into the gel, thus form a composite of the gel and fabric. The composite was then lyophilized. The resulting material was then cut into 2.5×1.5 cm pieces and tested in a swine spleen hemostasis model.

EXAMPLE 6

Hemostatic Performance of Materials in Porcine Splenic Incision Model

A porcine spleen incision model was used for hemostasis evaluation of lyophilized pads as prepared in Examples 1, 2, 4, and 5. A linear incision of 1.5 cm with a depth of 0.3 cm was made with a surgical blade on a porcine spleen. The pads (2.5×1.5 cm) were placed on the bleeding wound. After application of the test pad, digital tamponade was applied to the incision for 30 seconds. Additional applications of digital tamponade for 30 seconds each time were used until complete hemostasis was achieved. In certain embodiments, some of the pads were applied to wounds that had been pre-wet with saline. Table 1 lists the results of the evaluation.

TABLE 1

In Vivo Hemostasis of Fibrin(ogen) Pad

| Test Sample | Number of Compressions | Time to Hemostasis (seconds) |
|---|---|---|
| Example 5 | 1 | 30 |
| Example 5 | 1 | 30 |
| Example 5 | 2 | 75 |
| Example 2 | 2 | 90 |
| Example 2 | 2 | 75 |
| Example 2 (pre-wet) | 1 | 30 |
| Example 1 | 6 | 285 |
| Example 1 | 9 | 525 |
| Example 1 (pre-wet) | 6 | 245 |
| Example 4 | 3 | 105 |
| Example 4 | 2 | 65 |
| Example 4 (pre-wet) | 1 | 30 |
| Example 4 (pre-wet) | 2 | 75 |
| Example 4 (pre-wet) | 1 | 30 |

EXAMPLE 7

Preparation of Human Fibrinogen-Coated Surgicel®NuKnit and Fibrinogen-Coated Rayon for Platelet Binding Studies A 10×10 cm piece of Surgicel®NuKnit was laid flat on a stainless steel tray. 5 ml of a solution containing human fibrinogen as described in WO/02/095019 A1 at a concentration of about 50 mg/ml was pipetted onto the fabric and spread to evenly cover the fabric surface. The fluid slowly seeped into the fabric and precipitated, leaving a visible layer of precipitate on the fabric surface. The coated fabric was then frozen at −30° C. and the frozen solvent removed under vacuum and noted as Sample 7a. A control piece of non-oxidized rayon 10×10 cm was prepared in an identical manner and noted as Sample 7b. Both Samples 7a and 7b were tested for their ability to bind human platelets as described in example 8 and compared to an uncoated rayon control noted as Sample 7.

EXAMPLE 8

Platelet Binding Counts Measurement

A 2.5×2.5 cm piece of test fabric for each of samples 7, 7a and 7b was placed in a 3" diameter aluminum pan. 2 ml of platelet-rich plasma diluted in 5 ml of phosphate buffered saline was added to each piece of fabric and incubated at room temperature with gentle agitation on a lab-shaker table. Platelet counts were performed on the PRP using a Beckman Coulter AcT cell counter before and after reaction with fabric.

Fabrics were washed 3 times in 20 ml PBS pH 7.4, then fixed overnight with 2.5% gluteraldehyde. Fixed samples were rinsed for 10 minutes periods in solutions of 20%, 50% and 95% ethanol, respectively, then dried under vacuum. SEM was performed on dried samples. Table 2 lists the result of the evaluation.

TABLE 2

| SAMPLE | Platelet Count before reaction | Platelete Count post-reaction | Total Platelets Bound |
|---|---|---|---|
| Control | $259 \times 10^6$ | $240 \times 10^6$ | $19 \times 10^6$ |
| 7a | $518 \times 10^6$ | $404 \times 10^6$ | $114 \times 10^6$ |
| 7b | $518 \times 10^6$ | $464 \times 10^6$ | $54 \times 10^6$ |

EXAMPLE 9

Preparation of Human Fibrinogen-Coated Surgicel®NuKnit and Fibrinogen-Coated Rayon for Hemostasis Studies A 10×10 cm piece of Surgicel®NuKnit was laid flat on a stainless steel tray. 10 ml of a solution containing human fibrinogen at a concentration of about 50 mg/ml was pippetted onto the fabric and spread to evenly cover the fabric surface. The fluid slowly seeped into the fabric and precipitated leaving a visible layer of precipitate on the fabric surface. The coated fabric was then frozen at −30° C. and lyophilized and noted as Sample 9a. A control piece of non-oxidized rayon 10×10 cm was coated with fibrinogen in an identical manner and noted as Sample 9b. Both samples 9a and 9b were tested in a swine spleen hemostasis model as described in example 10

EXAMPLE 10

Hemostatic Performance of Materials in Porcine Splenic Incision Model

A porcine spleen incision model was used for hemostasis evaluation of lyophilized pads as prepared in Examples 9. A linear incision of 1.5 cm with a depth of 0.3 cm was made with a surgical blade on a porcine spleen. The pads (2.5×1.5 cm) were placed on the bleeding wound. After application of the test pad, digital tamponade was applied to the incision for 2 minutes. Additional applications of digital tamponade for 30 seconds each time were used until complete hemostasis was achieved. In certain embodiments, some of the pads were applied to wounds that had been pre-wet with saline. Table 3 lists the results of the evaluation.

TABLE 3

In Vivo Hemostasis Data of human Fibrinogen Coated Pad

| SAMPLE | Time to Hemostasis (minutes) |
|---|---|
| Sample 9b | 2.25 |
|  | 2.45 |
|  | 3.15 |
| Sample 9a | 2:00 |
|  | 2:00 |
|  | 2:00 |

We claim:

1. A method for making a medical device, comprising:
    providing a fabric substrate that comprises acid moieties;
    contacting said substrate with fibrinogen, fibrin or fibronectin in an acidic environment having a pH of from about 2.5 to about 6, where the acidic environment is provided by said acid moieties; and
    precipitating said fibrinogen, fibrin or fibronectin, whereby said precipitate is incorporated with said substrate.

2. The process of claim 1 wherein a gel comprising said fibrinogen, fibrin or fibronectin is contacted with said substrate.

3. The process of claim 2 wherein said gel comprises fibrinogen.

4. The process of claim 3 wherein said gel further comprises thrombin.

5. The process of claim 1 wherein a solution comprising said fibrinogen, fibrin or fibronectin is contacted with said substrate.

6. The process of claim 5 wherein said solution comprises fibrinogen.

7. The process of claim 2 wherein said substrate comprising said gel is lyophilized after formation of said precipitate.

8. The process of claim 5 wherein said substrate comprising said solution is lyophilized after formation of said precipitate solution comprises fibrinogen.

9. The process of claim 1 wherein said fabric substrate comprising acid moieties is oxidized regenerated cellulose having carboxylic groups and said precipitate is fibrinogen.

* * * * *